United States Patent
Chung et al.

(10) Patent No.: US 10,941,130 B2
(45) Date of Patent: Mar. 9, 2021

(54) MOLTEN SALT SYSTEM AND METHOD AND APPARATUS OF TRANSFORMATION FOR MULTI-CARBON PRODUCTION BY USING THE SAME

(71) Applicant: ACADEMIA SINICA, Taipei (TW)

(72) Inventors: Po-Wen Chung, Kaohsiung (TW); Prasenjit Bhaumik, Assam (IN); Hao-Ju Chou, New Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 16/362,172

(22) Filed: Mar. 22, 2019

(65) Prior Publication Data

US 2020/0299249 A1    Sep. 24, 2020

(51) Int. Cl.
| | | |
|---|---|---|
| C07D 307/46 | (2006.01) | |
| B01J 8/06 | (2006.01) | |
| B01D 3/10 | (2006.01) | |
| C01D 15/10 | (2006.01) | |

(52) U.S. Cl.
CPC ........... C07D 307/46 (2013.01); B01D 3/10 (2013.01); B01J 8/062 (2013.01); *B01J 2219/00051* (2013.01); *C01D 15/10* (2013.01)

(58) Field of Classification Search
CPC ............. C07D 307/46; B01J 8/062; B01J 2219/00051; B01D 3/10; C01D 15/10
USPC ................................................. 549/488
See application file for complete search history.

(56) References Cited

U.S. PATENT DOCUMENTS 4,590,283 A    5/1986 Rigel et al.

| 2013/0029383 A1 | 1/2013 | Pedersen et al. |
| 2014/0001399 A1 | 1/2014 | Lazzari et al. |

FOREIGN PATENT DOCUMENTS

| CN | 101333200 A | 12/2008 |
| CN | 102933567 A | 2/2013 |
| CN | 103459547 A | 12/2013 |

OTHER PUBLICATIONS

Rosatella et al, 5-Hydroxymethylfurfural (HMF) as a building block platform: Biological properties, synthesis and synthetic applications, Green chemistry, 2011, 13, 754-793 (Year: 2011).*

Prasenjit Bhaumik, Hao-Ju Chou, Ling-Chieh Lee, and Po-Wen Chung, Chemical Transformationfor5-Hydroxymethylfurfural Production from Saccharides Using Molten Salt System, ACS Sustainable Chem. Eng., 2018, 6 (5), pp. 5712-5717, published on Apr. 5, 2018, 21 pages.

Prasenjit Bhaumik, Hao-Ju Chou, Ling-Chieh Lee, and Po-Wen Chung, Poster Presentation on Jun. 28 and 29, 2018, Occasion: 36th Taiwan Symposium on Catalysis and Reaction Engineering conference, 3 pages.

* cited by examiner

*Primary Examiner* — Taylor V Oh
(74) *Attorney, Agent, or Firm* — Muncy, Geissler, Olds & Lowe, P.C.

(57) ABSTRACT

This invention relates to a novel molten salt system in chemical transformation of saccharides and a method as well as an apparatus for multi carbon production by the molten salt system. It is found that an eutectic molten salt composition is advantageous for multi-carbon productions through chemical transformation under mild conditions. This invention further provides a method and an apparatus for preparing 5-hydroxymethylfurfural (HMF) and HMF-derived chemicals from saccharides by the said molten salt system.

13 Claims, 4 Drawing Sheets

MOLTEN SALT SYSTEM AND METHOD AND APPARATUS OF TRANSFORMATION FOR MULTI-CARBON PRODUCTION BY USING THE SAME

TECHNICAL FIELD

This invention relates to a molten salt system in chemical transformation of saccharides and a method as well as an apparatus for multi carbon production by the molten salt system, and in particular to a method and an apparatus for preparing 5-hydroxymethylfurfural (HMF) and HMF-derived chemicals from saccharides.

TECHNICAL BACKGROUND

The greenhouse effect and depletion of oil reserves have driven intensified research on use of renewable resources in consumer products, including biomass raw materials in refining chemical raw materials. Among biomass-derived chemicals, 5-hydroxymethylfurfural (HMF) is considered as one of the most important platform chemical productions because it is regarded as a building block primarily for the synthesis of furan-based products analogous to those derived from petroleum industry. The United States has designated HMF as a "top 10+4" value-added bio-based chemical because it and its derivatives includes chemical intermediate products of 2,5-furandicarboxylic acid (FDCA), levulinic acid, 1,6-hexanediol, 2,5-dimethylfuran, 2,5-dimethyltetrahydrofuran, long chain alkanes, etc., which have a wide range of industrial applications in manufacturing commodity products.

Conventional HMF preparation methods suffer from low conversion and poor selectivity. The causes of low HMF production efficiency comprise the polymerization of HMF to form humins under a high temperature and in an acidic condition, hydrolysis of HMF to form levulinic acid under a high temperature and in acidic aqueous solution, and occurrence of a crossed aldol reaction between HMF and sugar to form humins under a high temperature. In other words, it is difficult to control side reactions triggered by heat. Thus, related downstream applications of HMF have yet to be successfully commercialized.

In recent years, considerable efforts have been made toward the transformation of carbohydrates into HMF due to its potential availability from carbohydrates such as fructose, glucose, cellulose, and inulin. For instance, Roquette (U.S. Pat. No. 4,590,283, 1986) discloses a method utilizing 20% fructose, dimethyl sulfoxide (DMSO) and AMBERLIT C200 cation resin as a catalyst for reaction at 80° C. for 8 hrs. to prepare HMF. Although a relatively high yield of HMF is achieved, HMF is manufactured in catalyst environment in these methods, in which a corrosive, expensive and nonreusable catalyst significantly increases the cost of the process. Separation of HMF from reaction solutions is another challenge in these methods requiring large amounts of organic solvents and considerable energy.

Given the above, the known methods have little potential for commercialization, and there is a need to provide a new process for manufacture of HMF under low reaction temperature with high reaction efficiency and selectivity. In comparison to other conventional systems involving either homogeneously or heterogeneously catalytic conversion for HMF, a catalyst-free and cost effective molten salt system might be advantageous.

Molten salts are crystalline solids at standard temperature and pressure that transform into a liquid phase at elevated temperature. Owing to that intrinsic properties, including high heat capacity and high thermal conductivity, molten salt systems are widely applied in solar energy harvesting, nuclear reactors, and fuel cells. In addition to these common applications, a molten salt system has been used for biomass carbonization into biochar and biocoal through supertorrefaction. However, the value of biocoal is not comparable to the energy input for biomass carbonization. Gasification/pyrolysis of biomass at >700° C. using a molten salt system has also been reported, but such process suffers from reactor corrosion, high cost of reactor design, low carbon selectivity, etc.

In the study of molten salts in renewable resources, hydrated $ZnCl_2$ was presented as effective media for cellulose chemical transformation to glucose, which is further hydrogenated to produce alcohol and alkane in the presence of catalysts in the same hydrated molten salt media. Various molten salt systems have been tested at a temperature of 400° C. or higher for pyrolysis of biomass into bio-oil consisting of numerous organic chemical. In addition, molten salt hydrate ($LiBr.3H_2O$) aqueous media has been reported for cellulose hydrolysis, furfural production as well as depolymerization of lignin, and few prior reports demonstrated the utilization of LiCl in the media of organic solvent or acid functionalized ionic liquids as well as Lewis acidic metal halide with ionic liquid for catalytic biomass conversion into HMF. However, these methods all employ catalysts and thus are accompanied with problems of high cost and catalyst recovery.

Accordingly, in a related aspect, it is an object of the invention to provide a method for producing biomass-derived chemicals in the absence of a catalyst or a large amount of organic solvents. It is another object of the invention to solve low conversion and selectivity when manufacturing biomass-derived chemicals, especially HMF. It is another object of the invention to provide a method for production of HMF under lower reaction temperature with reduced by-product. These and other objects are achieved by the eutectic molten salt system and the method as well as the apparatuses for processing saccharides according to the present invention.

SUMMARY

We discovered a new molten salt system in chemical transformation of saccharides. More specifically, we discovered a new molten salt system in chemical transformation of biomass-derived saccharides for multi-carbon products, such as furfural, HMF and HMF dimer. The molten salt system is capable of transforming various saccharides into a biomass-derived chemical, such as HMF, under different reaction conditions, for example in absence of any additional catalyst. Moreover, the molten salt is recovered and re-used in multi recycle runs without compromising its activity. We also provide simple methods for easy separation of the multi-carbon products, which would minimize side reactions, such as degradation.

In a first aspect, the invention provides a new molten salt system for chemical transformation at low temperature. The molten salt system is preferably a eutectic molten salt composition possessing a low eutectic point under 200° C., wherein the eutectic molten salt composition comprises at least two salts.

In a second aspect, the invention provides one new application of the molten salt system having low eutectic point for organic chemical transformation from saccharides for multi-carbon products at low temperature. In particularly, the invention relates to chemical transformation for 5-Hydroxymethylfurfural (HMF) production from saccharides using the eutectic molten salt system.

One embodiment of the invention is chemical transformation for HMF production from saccharides using the eutectic molten salt system comprising at least one lithium salt. One embodiment of the invention is chemical transformation for HMF production from saccharides using a ternary eutectic molten salt system. One embodiment of the invention is chemical transformation for HMF production from saccharides using the eutectic molten salt system comprising a lithium salt, a sodium salt, and a potassium salt. One embodiment of the invention is chemical transformation for HMF production from saccharides using $LiNO_3$—$NaNO_3$—$KNO_3$ (LSP) ternary eutectic molten salt system.

In a third aspect, the invention provides a continuous process for preparing HMF or a HMF derivate from saccharides using the molten salt system, preferably the eutectic molten salt system.

In a fourth aspect, the invention provides an apparatus for the continuous process for preparing HMF or a HMF derivate from saccharides using the eutectic molten salt system.

BRIEF DESCRIPTION OF THE DRAWINGS

FIG. 2a relates to fructose chemical transformation.

FIG. 2b relates to glucose chemical transformation.

DETAILED DESCRIPTION

Figure 1:
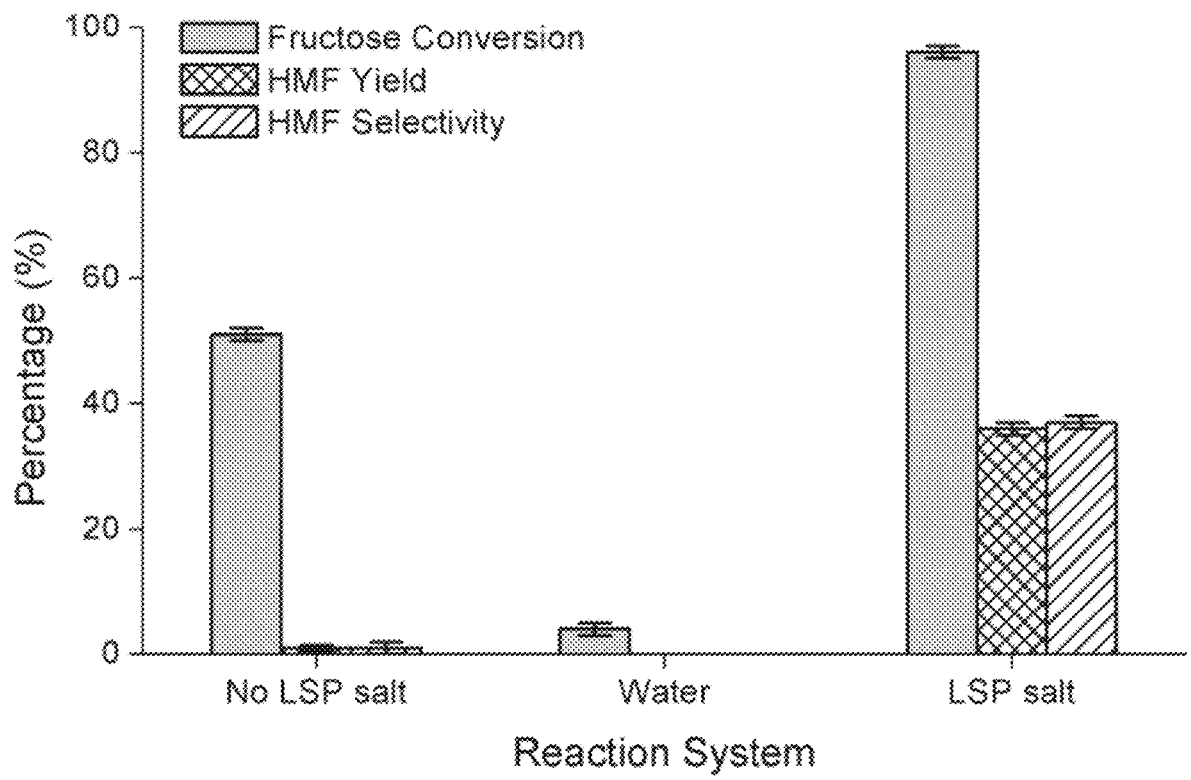
FIG. 1 is a bar chart indicating chemical transformation of fructose into HMF with different systems. The transformation is conducted at 135° C. for 30 mins.

The following is a description of the present invention, including preferred embodiments thereof, given in general terms. The following detailed description is merely exemplary in nature and is not intended to limit the various embodiments or the application and uses thereof. Furthermore, there is no intention to be bound by any theory presented in the preceding background or the following detailed description.

Throughout this specification and any claims which follow, unless the context requires otherwise, the words "comprise," "comprising" and the like, are to be constructed in an inclusive sense as opposed to an exclusive sense, that is to say, in the sense of "including, not limited to."

"Biomass" as referred to herein comprises any material originally of biological origin that comprises saccharides capable of being used as a renewable nonfood feedstock. In particular embodiments, the biomass is lignocellulosic biomass that is selected from the group consisting of plant material, grass, wood, agricultural wastes, organic waste, etc. Examples of lignocellulosic biomass include cellulose, hemicellulose and lignin.

Molten Salt System

The molten salt system is a molten salt composition comprising at least two different salts that are homogeneously mixed. The molten salt composition preferably is a eutectic molten salt composition and has a low eutectic point under 200° C., preferably under 175° C., more preferably under 150° C.

In an embodiment, the eutectic molten salt composition is a ternary molten salt composition. In an embodiment, the eutectic molten salt composition comprises at least one alkali metal salt selected from the group consisting of lithium salts, sodium salts, and potassium salts. In an embodiment, the eutectic molten salt composition comprises at least one lithium salt. In an embodiment, the eutectic molten salt composition comprises at least two alkali metal salts selected from the group consisting of lithium salts, sodium salts, and potassium salts. In an embodiment, the eutectic molten salt composition comprises a molten salt melt of a lithium salt, a sodium salt, and a potassium salt. In a particular embodiment, the eutectic molten salt composition comprises $LiNO_3$—$NaNO_3$—$KNO_3$ (LSP) molten salt melt.

In a particular embodiment, at least one of the alkali metal salts is selected from the group consisting of nitrates, nitrites, sulfates, chlorides, and carbonates, preferably nitrates and nitrites, and more preferably nitrates.

In an embodiment where a lithium salt is present, the lithium salt and the rest of the salts are mixed in a weight ratio from 1:1 to 1:3, preferably 1:2 to 1:3, and more preferably 1:2.5 to 1:2.9.

In an embodiment where the eutectic molten salt composition comprises a lithium salt, a sodium salt, and a potassium salt simultaneously, the lithium salt, the sodium salt, and the potassium salt are in a weight ratio from 1:0.5:0.5 to 1:1:2, preferably 1:0.5:1.5 to 1:1.5:1.5, and more preferably 1:0.7:1.8 to 1:0.8:2.1.

To prepare the molten salt system, a preferred ratio of the molten salts is homogeneously mixed and ground by mortar and pestle. In an embodiment, the molten salt system is in the eutectic state.

Chemical Transformation of Saccharides

The inventors surprisingly find that low temperature of a molten salt system would carry out chemical transformation of saccharides in a liquid phase, which could offer better carbon selectivity, even in the absence of catalyst. Therefore, a new application of molten salt system with low eutectic point is developed in chemical transformation from saccharides at low temperature.

It is speculated that the activity of chemical transformation from saccharides for lower multi-carbon compounds is due to specific high heat capacity of the molten salts. Due to high heat capacity and high thermal conductivity of molten salt, molten salt melts would exhibit homogeneous heat and mass transfer to carry out chemical transformation even at low temperature. However, high heat capacity may not be the sole contribution to chemical transformation of saccharides of the invention. A molten salt system could not only facilitate the hydrolysis of saccharides into mono-saccharide, but also could promote isomerization and further dehydration. It is believed that the unique acid-base pair of molten salt melts with oxyanions could be responsible for the dehydration and isomerization of saccharides, especially mono-saccharides. In addition, the presence of alkali metal cations in salt melt could perturb the structure of saccharide molecules by providing affinity towards saccharide oxygen atoms. This structural perturbation could alter saccharide molecules in low energy conformations, which eventually ease the process of its transformation. Depending on the chemicals to be obtained, any saccharide could be suitable for transformation by the eutectic molten salt system.

The eutectic molten salt system of the invention is favorable for production of 5-hydroxymethylfurfural (HMF) and the derivatives thereof. Owing to the unique property of the acid-base pair and molecular perturbation of saccharides by small cation of molten salt melts, the formation of HMF is presented under milder conditions using the eutectic molten salt system in absence of any additional catalyst. It is further found that a eutectic ternary molten salt system having a eutectic point under 200° C. according to the invention is favorable for HMF production. In addition, a eutectic ternary nitrate molten salt system according to the invention is more favorable for HMF production, such as a $LiNO_3$—$NaNO_3$—$KNO_3$ (LSP) molten salt melt. It is believed that high specific heat capacity (1.54 Jg−1K−1) of LSP molten salt melt contributes to the activity of chemical transformation for HMF because elimination of 3 molecules of water per monosaccharide unit is required to yield HMF from saccharides. However, chemical transformation is not governed by high heat capacity only.

The eutectic molten salt system of the invention can transform various saccharides such as mono-saccharide (fructose and glucose), di-saccharide (cellobiose), chitin, chitosan, glucosamine, N-acetyl glucosamine, and poly-saccharide (starch and microcrystalline cellulose) into HMF. Preferred saccharides for the formation of HMF and the derivatives thereof are monosaccharides, disaccharides, and polysaccharides. More preferred saccharides for the formation of HMF and the derivatives thereof are monosaccharides having 5 or 6 carbon atoms, such as fructose and glucose, and disaccharides and polysaccharides derive therefrom, such as saccharide, inulin, cellobiose, cellulose, and starch Among these, fructose and glucose are preferred feeds for HMF production. Scheme 1 shows that direct conversion of biomass-derived saccharides into HMF through LSP molten salt system at low temperature in absence of additional catalyst is promising. In the case using monosaccharides having 5 carbon atoms, such as xylose, and disaccharides and polysaccharides derive therefrom, the saccharide may be firstly transformed into furfural and then be propagated into C6 or higher products, such as HMF, in the presence of an additional carbon resource.

The eutectic molten salt system of the invention, such as the aforementioned LSP molten salt melts, can intrinsically transforms fructose into HMF. The temperature of the transformation reaction is from about 20° C. to 200° C., preferably from about 25° C. to 180° C., more preferably from about 80° C. to 160° C., and most preferably from about 115° C. to 155° C. In addition, depending on the chemical products to be obtained, it is suggested that the transformation reaction be processed at a specific temperature of 110 to 120° C., 120° C. to 130° C., 130° C. to 140° C., or 140° C. to 150° C. The reaction time is from 15 minutes to 150 minutes, preferably from 20 to 120 minutes, more preferably from 30 to 120 minutes, more preferably from 30 to 90 minutes, and more preferably from 45 to 60 minutes. It is suggested that the reaction be carried out at 100° C. to 125° C. for 35 to 45 minutes, or at 135° C. for 30 minutes, or 145° C. for 30 minutes. The best mode of the reaction was carried out at 135° C. for 30 minutes. Under proper reaction conditions, the fructose conversion is at least 90%, at least 95%, at least 96%, or at least 97%, while the selectivity of HMF production could reach at least 30%, at least 35%, at least 40%, at least 50%, or even at least 60%. Glucose (isomeric product of fructose) may also be observed in the aforementioned reaction.

Fructose transformation reactions in the LSP molten salt system at different temperatures and reaction time course have been studied. It is possible to have shorter time course for similar fructose conversion and HMF selectivity while the reaction temperature was elevated up. Take the following as an example. When reactions were carried out at 125° C. for 30 min, fructose was converted into HMF within ca. 17% selectivity at 56% conversion. Both fructose conversion (ca. 95%) and HMF selectivity (ca. 37%) could be enhanced by increasing the reaction time to 45 min at 125° C. Similar fructose conversion (ca. 96%) and HMF selectivity (ca. 37%) can be achieved within shorter time course of 30 min by elevating the reaction temperature to 135° C.

Unlike the direct chemical pathway of dehydration required from fructose, HMF evolved from glucose requires isomerization, prior to further dehydration as reported in a previous study with regards to acid catalyzed processes. Therefore, lower glucose conversion and HMF formation might be expected. Interestingly, the inventors surprisingly find that through the molten salt system of the invention, HMF yield escalated 7-fold with a 1.75-fold increase of glucose conversion, when the reaction was carried out at 125° C. from 30 to 60 min, and glucose conversion was further increased to 76% with similar HMF selectivity when reaction time was further increased to 120 min. In addition, when the reaction was carried out at 135° C. from 30 to 60

Scheme 1. Novel strategy of HMF production from various saccharides using LSP molten salt system.

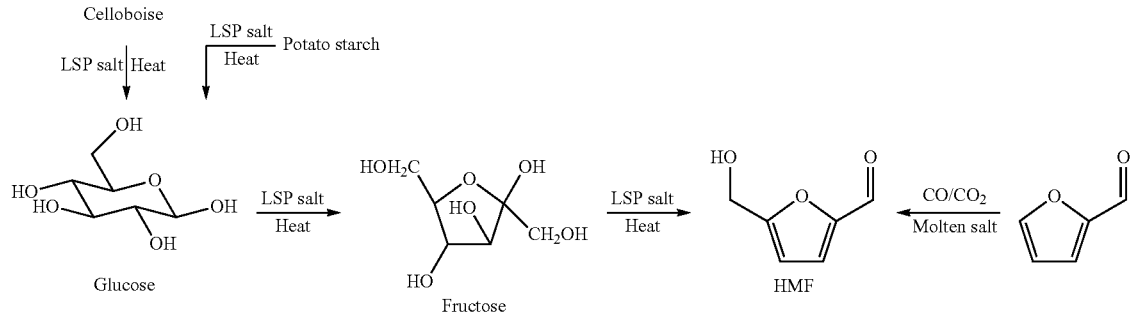

mins, HMF selectivity remained almost the same while glucose conversion increased from 50% to 77%. For comparison, when glucose transformation was carried out using pure nitrate anionic ionic liquid (IL), i.e. 1-ethyl-3-methylimidazolium nitrate [EMIM]$NO_3$ was used to transform glucose at 135° C. for 30 min, it turned out that only 24% glucose was lost without any observed isomeric product (fructose) or dehydration product (HMF). Above all, it suggests that the molten salt system of the present invention not only facilitates the dehydration of saccharides, but also participates in the isomerization of glucose to fructose.

Apart from the mono-saccharide, chemical transformation of cellobiose, disaccharide of D-β-glucose through 1,4 β-glycosidic linkage, in the molten salt system of the invention was also tested. After reaction, various products from dehydration of cellobiose were observed, such as glucose, fructose, and HMF. This result suggests that successive hydrolysis of cellobiose to glucose followed by isomerization of glucose to fructose and then dehydration of fructose into HMF is possible by using this molten salt system. In addition, potato starch, polysaccharide of glucose linked through α-glycosidic bond, was chemically converted into HMF, glucose by using the molten salt system of the invention. Apparently, the molten salt system of the invention is able to transform polysaccharides into HMF directly without any additional acid catalyst.

Continuous Process

Molten salts are known as having severe corrosion on metals or reactors due to their high eutectic point and high operation temperature, and thus are usually considered not suitable for a continuous process. However, having the low eutectic point, the molten salt system of the invention overcomes the prejudice and can be applied to a continuous process for multi-carbon productions.

The inventors also developed a process for chemical transformation for 5-Hydroxymethylfurfural (HMF) production by using the molten salt system of the invention, in particular the eutectic molten salt system. The process comprises steps of mixing a saccharide with an eutectic molten salt composition of the present invention in a liquid phase to form a mixture; heating the mixture of the saccharide and the eutectic molten salt composition at a reaction temperature for a desired reaction time; cooling the mixture to room temperature; and extracting HMF from the mixture Salts for the eutectic molten salt composition are homogeneously mixed and ground by mortar and pestle prior to use in reaction. The eutectic molten salt composition is preferably preheated so that it would transform into the liquid phase.

The saccharide to be transformed (substrate) is in an amount up to 1 wt. %, 2 wt. %, 5 wt. %, 8 wt. %, or 10 wt. % based on the total weight of the eutectic molten salt composition, preferably up to 5.0 wt. %, and more preferably up to 2.0 wt. %.

Common heating methods are suitable for the heating step in the aforementioned process for HMF production, such as oil bath, water bath, etc. Pre-heating the heating medium is suggested so that the mixture of the saccharides and the eutectic molten salt composition are heated and transformation proceeds at a consistent temperature.

Dark brown and tarry carbonaceous product was commonly observed when the aforementioned reactions were either carried out at longer reaction time or at elevated temperatures. Moreover, trace amount of HMF rehydration products (formic acid and levulinic acid) were identified in saccharide transformation using the molten salt system. In order to rule out unwanted transformation of HMF, effective separation is necessary.

To enhance HMF production through organic solvent extraction, 2-sec-butylphenol (SBP) solvent, which was reported to extract HMF from aqueous phase efficiently and minimize HMF degradation and condensation, was employed. In a process for HMF formation from fructose using the LSP molten salt melts at low temperature (125° C.), addition of SBP solvent enhances fructose conversion by 1.3-fold, HMF yield by 3-fold and HMF selectivity by 2.2-fold in comparison to reaction with only LSP molten salt melts at 125° C. SBP solvent can extract ca. 70% HMF (of total HMF formed in reaction) from LSP molten salt composition. Compared to other frequently used solvents for HMF extraction from aqueous phase like methyl iso-butyl ketone (MIBK) and toluene, HMF yield is merely ca. 5% in the case of MIBK, and 18% in the case of toluene. This observation of less HMF production suggests that those solvent are not efficient in HM F extraction from pure LSP molten salt melts. Experiments indicated that SBP acts only as an extracting solvent while keeping HMF stable.

Figure 3:
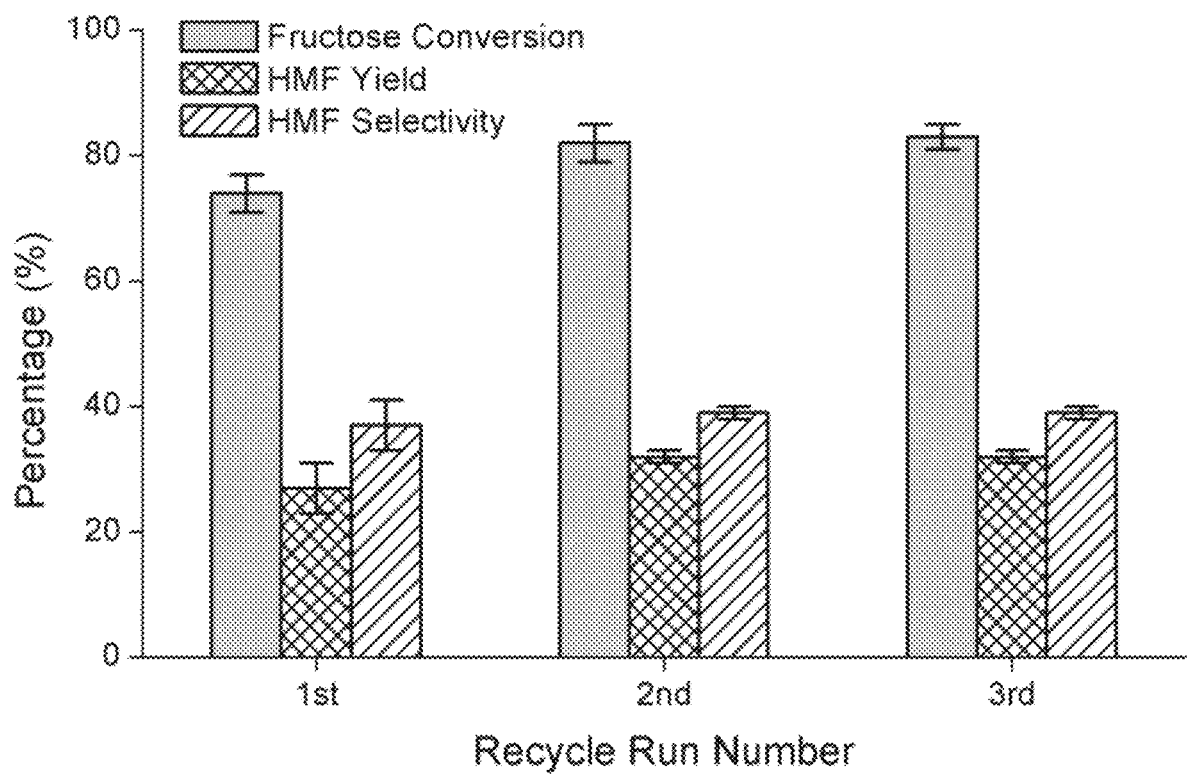
FIG. 3 is a bar chart showing results of recycle experiments of LSP molten salts for fructose transformation.

For a recyclability study, LSP molten salt was recovered from reaction solution after extraction of HMF in SBP solvent. The recycle study was carried out using fructose as a substrate, and the conversion, yield and selectivity were measured by normalizing remaining fructose and HMF in recovered LSP molten salt. It is noteworthy that, in batch reaction, LSP molten salt was recycled at least 3 times without losing its activity at 125° C., 30 min (FIG. 3). Thus, using molten salts possessing low eutectic point, such as LSP molten salt melts, could be regarded as one alternative process for the conversion of biomass-derived chemicals.

However, there is still a need for direct separation of HMF for continuous processing. Taking as an example, a chemical transformation of glucose for HMF production with an LSP molten salt system, decomposition products from HMF, such as 5,5'-(oxybis(methylene)) bis(furan-2-carbaldehyde) (HMF dimer), are easily observed as minor products of the reaction. This formation of HMF dimer could result from the prolonged aging process during the reaction. It is believed that rapid aging and decomposition of pure HMF would take place through intermolecular etherification, and oligomerization of HMF would occur and produce higher molecular weight compounds with number of furan cores resulting in formation of oligomer, such as HMF dimer. Therefore, to reduce undesired side products, HMF needs to be separated from the reaction zone as soon as possible.

Considering the chemical transformation of the invention only involves saccharides, the eutectic molten salt system, and chemical products of dehydration, the significant differences between boiling points of these materials could be a solution for separation. A vacuum distillation system can not only easily separate chemical products during the transformation process of saccharides, but also minimize HMF degradation owing to the said efficient separation.

For the downstream process, the invention could be expanded to fix carbon dioxide while providing furfural/HMF and HMF-derived chemicals. Carbon dioxide ($CO_2$) or Carbon monoxide (CO) could be used as an alternative carbon source for propagating C5 chemicals, such as furfural, to C6 or higher chemicals (HMF or HMF dimer, or furfural/HMF derivatives) through a molten salt system. In addition, various organic chemicals may be produced through the molten salt system. For example, by adding oxygen gas, the HMF transformed from the saccharides can be further transformed into 2,5-Furandicarboxylic acid (FDCA) in the presence of oxygen gas, Moreover, C6+ chemicals can be easily produced by addition of $CO_2$ through the double bond of HMF obtained from the molten salt system and separated by vacuum distillation.

Apparatus

Figure 5:
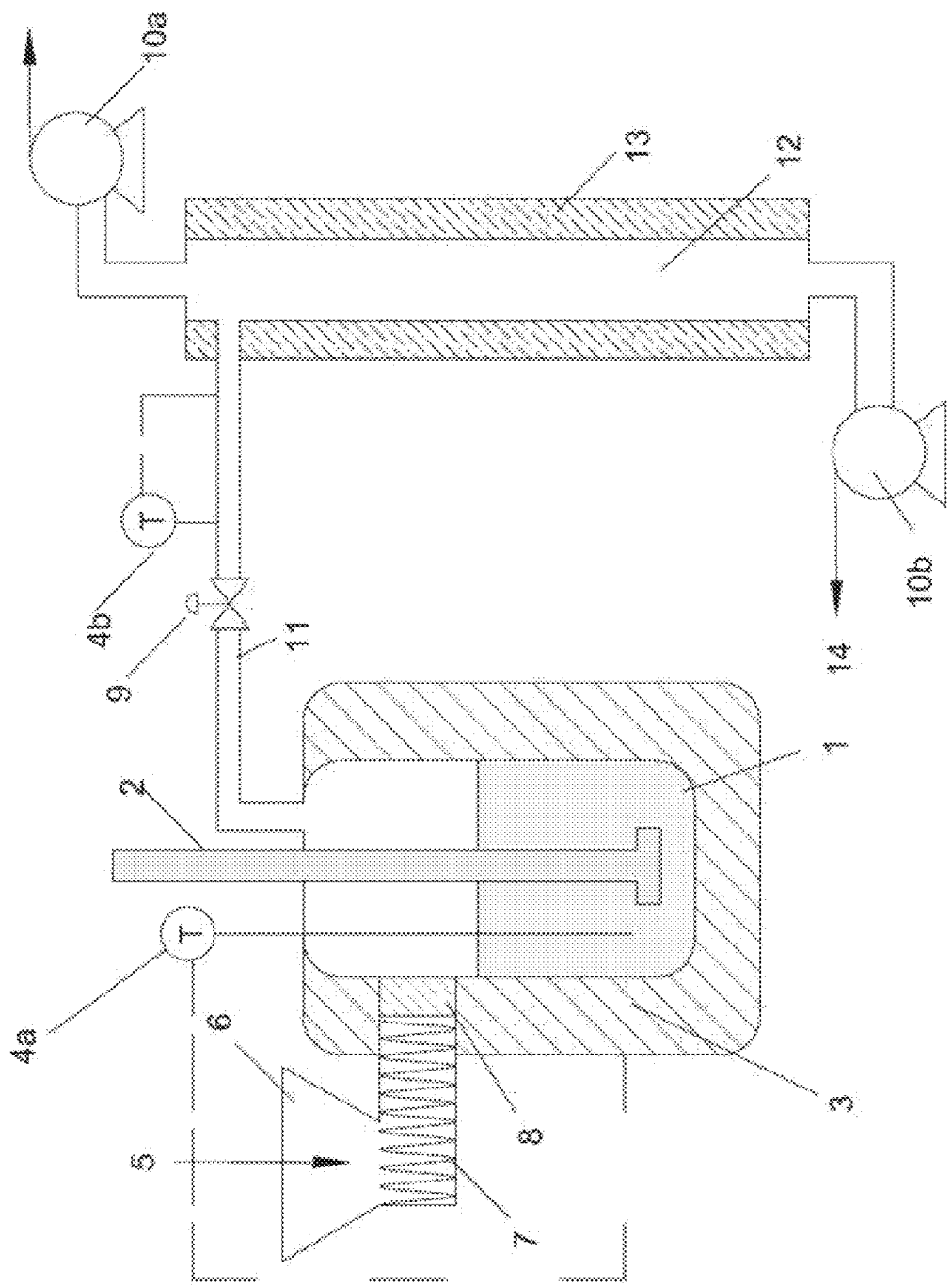
FIG. 5 is a simplified diagram of an exemplary continuous process for HMF production.

A working example of the reaction apparatus as well as the vacuum distillation apparatus for chemical transformations according to the invention is illustrated in FIG. 5, demonstrating the continuous process as described.

A reaction vessel 1 shown in FIG. 5 is embedded in a furnace 3 with a temperature range from 25° C. to 200° C., controlled by a first temperature controller 4a, The average reaction time is from 20 to 120 minutes. A continuously stirred agitator 2 regulates the reactions. Feedstock 5 is pushed into the reaction vessel 1 via a funnel 6 and a screw pump 7. Once feedstock 5 enters the reaction vessel 1, a gate 8 will open, dropping the feedstock 5 into the vessel 1 and close when it becomes full.

After the reaction finishes, the gate 8 and a reverse valve 9 open, allowing a first vacuum pump 10a to draw the products into a vacuum distillation tower 12 via a pipeline 11, monitored by a second temperature controller 4b. As the products cool via a cooler 13, different final products such as to 5-hydroxymethylfurfural (HMF), HMF dimer and/or HMF derivative 14 can be extracted via a second vacuum pump 10b.

Figure 6:
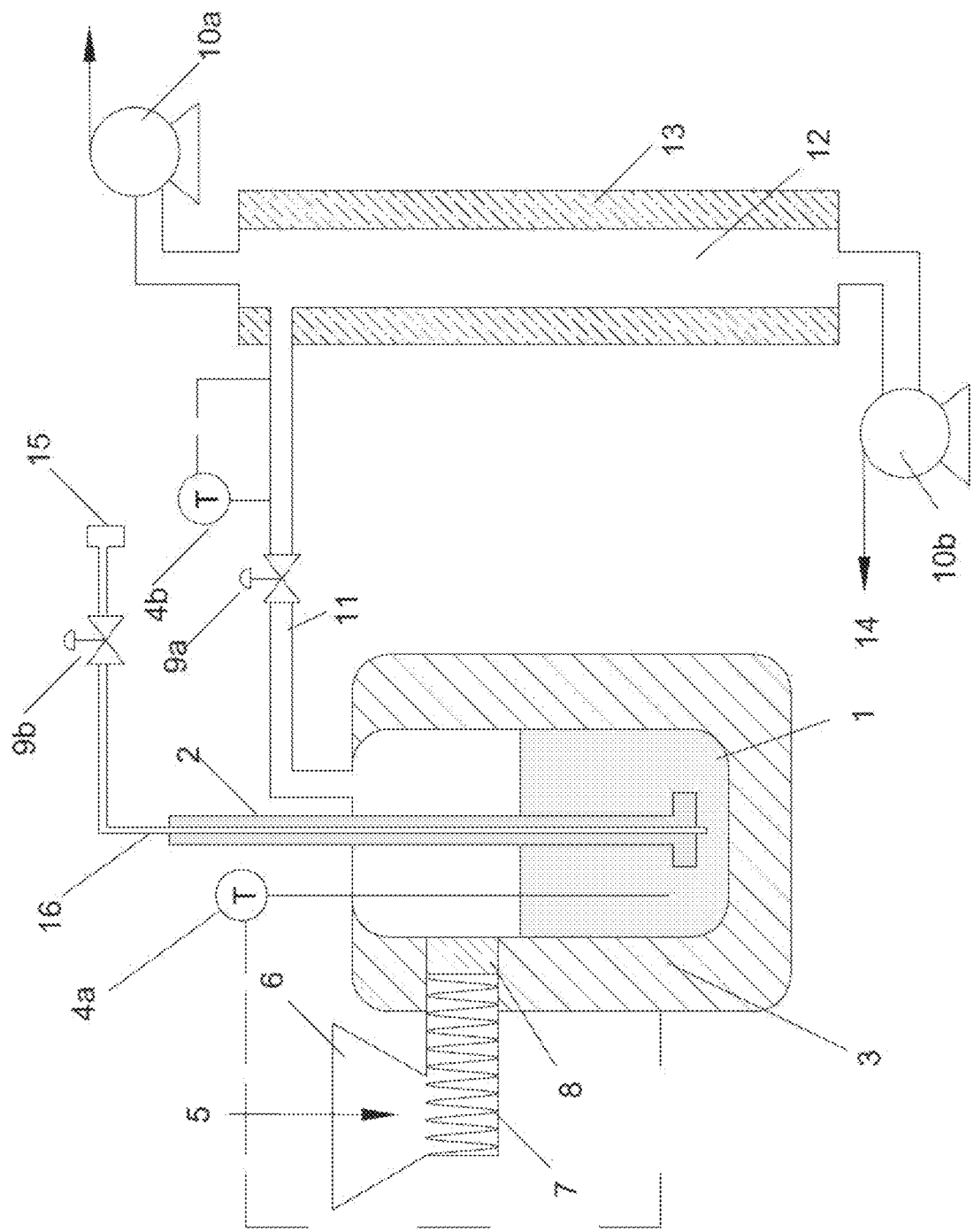
FIG. 6 is a simplified diagram of an exemplary continuous process for HMF production with gas tank.

The reaction vessel 1 shown in FIG. 6 is embedded in a furnace 3 with a temperature range from 25° C. to 200° C., controlled by the first temperature controller 4a. The average reaction time is from 20 to 120 minutes. A continuously stirred agitator 2 along with a gas injector 16 and a reverse valve 9b regulate the reactions. An interchangeable gas tank 15 allows various gases to be used. Feedstock 5 is delivered into the reaction vessel 1 via a funnel 6 and a screw pump 7. Once feedstock 5 enters the reaction vessel 1, a gate 8 will open, dropping the feedstock 5 into the vessel 1 and close when it becomes full.

After the reaction is finished, the gate 8 and a reverse valve 9a open, allowing a first vacuum pump 10a to draw the products into a vacuum distillation tower 12 via a pipeline 11, monitored by a second temperature controller 4b. As the products' cool via a cooler 13, different final products such as to 5-hydroxymethylfurfural (HMF), HMF dimer, and/or HMF derivative 14 can be extracted via a second vacuum pump 10b.

EXAMPLES

Example 1: Transformation of Fructose into HMF

Molten salt composition, lithium nitrate (97%, J.T.Baker® Chemicals, USA), sodium nitrate (99%, J.T.Baker® Chemicals, USA), and potassium nitrate (99%, J.T.Baker® Chemicals, USA) salts were homogeneously mixed in a weight ratio of 25.92/20.01/54.07 and ground by mortar and pestle prior to use in reaction. This eutectic ternary salt composition is denoted as LSP. Saccharide molecules (40 mg) and LSP molten salt (2 g) were mixed well in a glass tube reactor. The glass tube reactor was then placed in a pre-heated oil bath under 500 rpm stirring and was heated to process the reaction. After reaction, the tube reactor was cooled to room temperature.

Fructose (>99%, Sigma-Aldrich, USA) transformation reactions in LSP molten salt system at different temperatures and reaction time course have been studied. When reactions were carried out at 125° C. for 30 min, fructose was converted into HMF within ca. 17% selectivity at 56% conversion. Both fructose conversion (ca. 95%) and HMF selectivity (ca. 37%) could be enhanced by increasing the reaction time to 45 min at 125° C. Similar fructose conversion (ca. 96%) and HMF selectivity (ca. 37%) can be achieved within shorter time course of 30 min by elevating the reaction temperature to 135° C.

The experimental results shown in FIG. 1 indicate that LSP molten salt melts intrinsically transform fructose into HMF. They show that when the reactions were carried out at 135° C. for 30 minutes, HMF production could reach 37% selectivity out of 97% fructose conversion after reaction. Glucose (isomeric product of fructose) was also observed in the aforementioned reaction.

To understand the influence of LSP molten salt melts, a control experiment for fructose was conducted under the same condition, albeit in the absence of LSP molten salt composition. Control experiments included fructose conversions in water or fructose solely under the same reaction conditions, 30 mins at 135° C. Reaction conditions: fructose (40 mg), no LSP molten salt (0 g salt), water (4 mL), or LSP molten salts (2 g). Experimental results are shown in FIG. 1, where "No LSP molten salt" refers to the control experiment not using LSP molten salt, and "water" refers to the control experiment carried out in water without using LSP molten salts. The results suggest that water can neither convert fructose into other chemicals (conversion<4%) nor promote HMF production from fructose, and that negligible HMF formation was observed at fair fructose conversion (51%) with bulk fructose.

Example 2: Transformation of Different Saccharides into HMF

Glucose (>99.5%, Sigma-Aldrich, USA) is tested under the same reaction conditions described in Example 1 but with various reaction temperatures and reaction times. Results show that HMF yield of escalated 7-fold higher with the 1.75-fold increase of glucose conversion when the reaction was carried out at 125° C. from 30 to 60 min. When reaction time was increased to 120 min, a slight increase in glucose conversion (up to 76%) was observed with similar HMF selectivity (ca. 13%). When the reaction temperature was elevated to 135° C. for 30 min, HMF selectivity was reported as 16% at 50% glucose conversion, which remained similar but with increased glucose conversion (77%) when the reaction was carried out for 60 min.

For control experiments, both saccharide solution and bulk saccharide were tested without LSP molten salt under similar reaction conditions. Control experiments with glucose solution or bulk glucose were carried out at 125° C. for 120 min, and the results showed that not only was HMF formation not observed, but also negligible glucose was converted in the absence of LSP molten salt. Likewise, no detectable HMF was observed with less than 14% glucose conversion in the control experiment at 135° C.

Apart from the mono-saccharide chemical transformation by using the molten salt system of the present invention, cellobiose (>98%, Sigma-Aldrich, UK), disaccharide of D-β-glucose through 1,4 β-glycosidic linkage was used as the substrate in the LSP molten salt system. Cellobiose transformation was carried out at different temperatures (125° C., 135° C., 145° C. and 155° C.) for various time courses (15 min, 30 min and 60 min). Cellobiose was converted at 51% and glucose, fructose, and HMF were found in the product under moderate conditions (135° C., 30 min), while a negligible amount of cellobiose transformation (<4%) could be found in the control experiment. This result suggests that successive hydrolysis of cellobiose to glucose, followed by the isomerization of glucose to fructose then dehydration of fructose into HMF is possible by using this LSP molten salt system. In addition, potato starch (Sigma-Aldrich, USA), polysaccharide of glucose linked through α-glycosidic bond, was chemically converted into HMF, along with glucose and fructose by using LSP molten salt at 145° C. and 155° C. for 150 min. The data suggest that an LSP molten salt system can transform polysaccharides into HMF directly without any additional acid catalyst.

Example 3: Comparison of Reactivity Using Nitrate Molten Salt and Nitrate Ionic Liquid in Saccharide Chemical Transformation We tested the reactivity of nitrate anionic ionic liquid (IL), i.e. 1-ethyl-3-methylimidazolium nitrate [EMIM]$NO_3$ (M.P.=41° C.) (>98%, TCI, USA) in comparison to nitrate molten salts, i.e. LSP molten salt (M.P.=118° C.), to understand the influence of the eutectic molten salts system of the present invention. For control experiments with IL, saccharide (40 mg), such as fructose and glucose, and IL (2 g) were mixed in a glass liner and heated in an oil bath at 135° C. for 30 min and processed according to the previous method described in Example 1. The experiments with nitrate molten salts melts were conducted under the same reaction conditions described in Example 1.

Figures 2A, 2B:
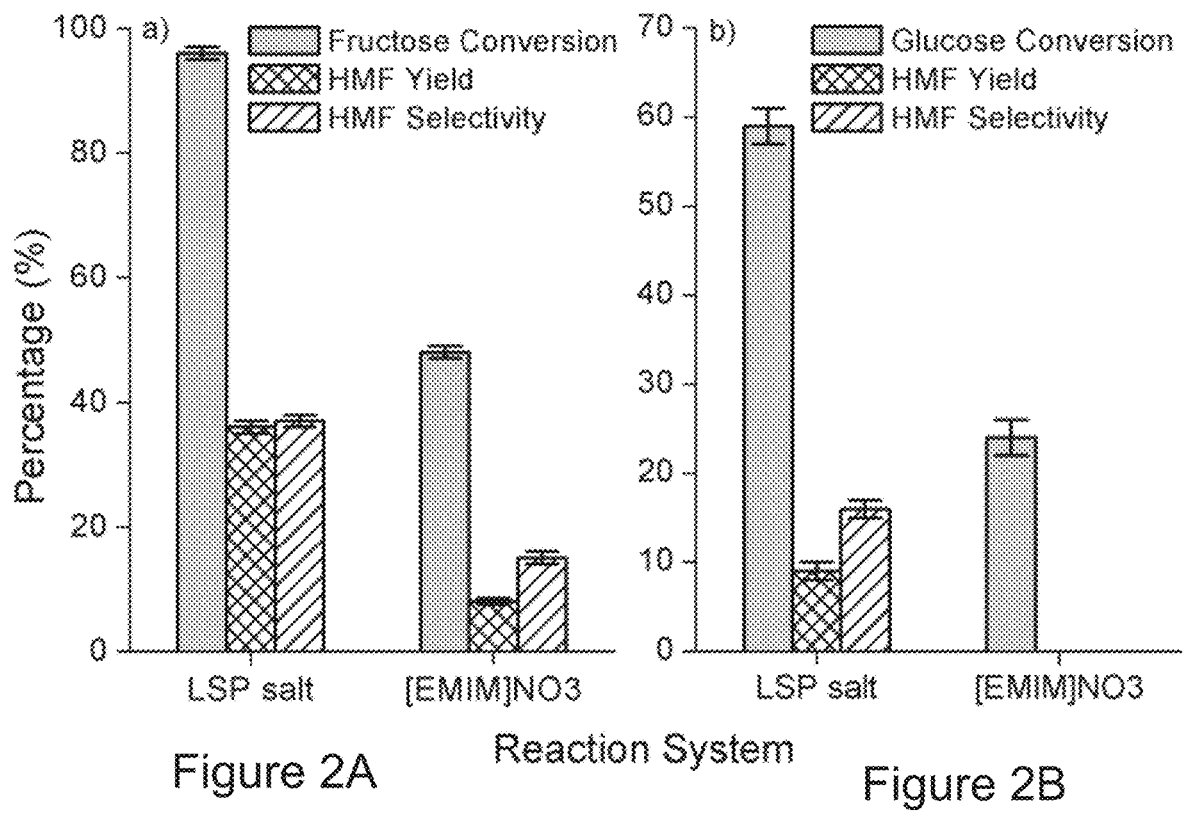
FIG. 2a is a bar chart relating to comparison of reactivity using nitrate molten salt and nitrate ionic liquid in saccharide chemical transformation.
FIG. 2b is a bar chart relating to comparison of reactivity using nitrate molten salt and nitrate ionic liquid in saccharide chemical transformation.

As shown in FIG. 2a, LSP molten melts exhibited 4.5-fold higher of HMF production than pure [EMIM] $NO_3$ system with 2-fold higher of fructose conversion within 30 min at 135° C. In the case of glucose transformation (FIG. 2b), the conversion of glucose was about 60% with HMF selectivity of about 16% in the LSP molten salt system, while only 24% glucose was converted in the [EMIM] $NO_3$ system without any isomeric product (fructose) or dehydration (HMF) product. Given the above, the eutectic molten salt system of the present invention apparently exhibits better efficacy on chemical transformation of saccharides for HMF production and could offer an alternative process for HMF production.

Example 4: Recycle Experiment

To understand the influence of organic solvents on the LSP molten salts for HMF extraction, experiments were conducted by placing fructose (40 mg), LSP molten salt (2 g), and organic solvent (1 mL) in a glass tube reactor at low temperature (125° C.). At such temperature, experiments show that conversion of fructose with the LSP molten salts solely is about 56%.

Figure 4:
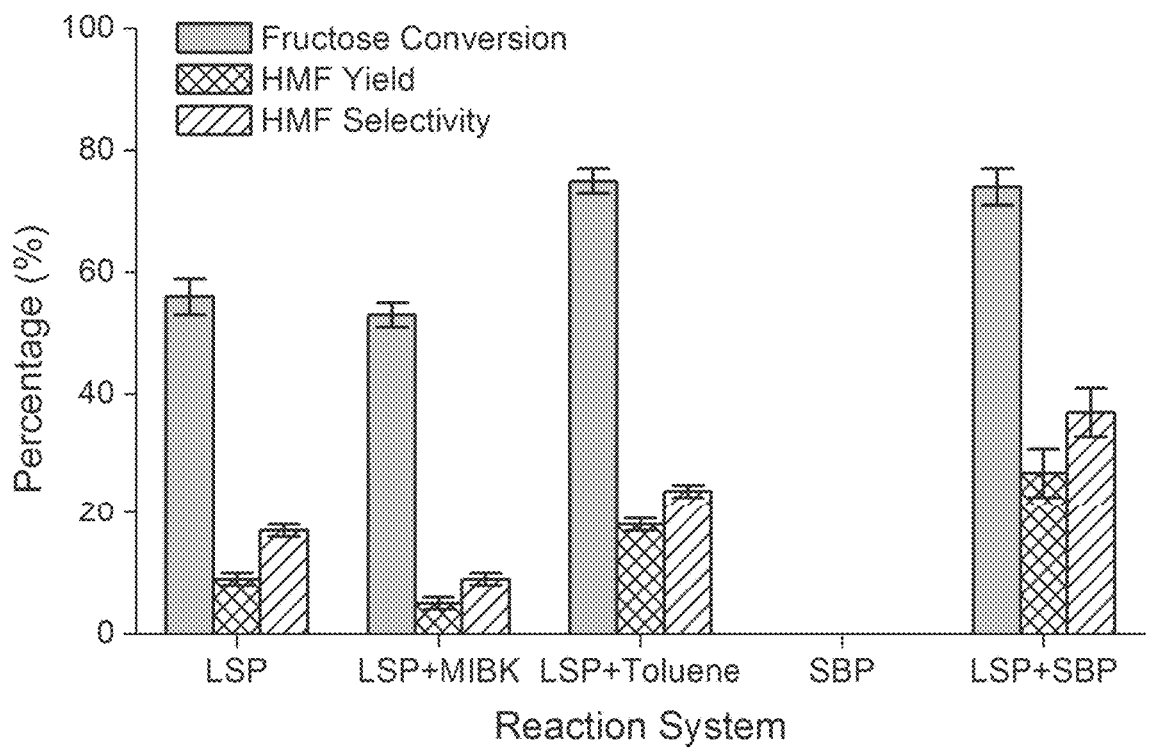
FIG. 4 is a bar chart illustrating influence of organic solvent extraction of HMF in fructose chemical transformation using LSP molten salt.

Tested organic solvents include 2-sec-butylphenol (SBP, 98%, Alfa Aesar, UK) solvent, methyl iso-butyl ketone (MIBK), and toluene (99.9%, Duksan Pure Chemicals Co. Ltd., Korea). We have noticed that an addition of SBP solvent indeed enhanced fructose conversion by 1.3-fold, HMF yield by 3-fold and HMF selectivity by 2.2-fold in comparison to the reaction with only LSP molten salt (fructose conversion: ca. 56%, HMF yield: ca. 9% and HMF selectivity: ca. 17%) at 125° C., 30 min (FIG. 4). In addition, SBP solvent can extract ca. 70% HMF (of total HMF formed in reaction) from a LSP salt solution. However, the HMF yields of MIBK and toluene were ca. 5% and ca. 18%, respectively. This result suggests that those solvents are not efficient in HMF extraction (MIBK: ca. 20% and toluene: ca. 3%) from pure LSP molten salt melts.

For recycle study, LSP molten salt was recovered from reaction solution after extraction of HMF in SBP solvent. The recycle study was carried out using fructose as the substrate and the results of the conversion, yield, and selectivity were measured by normalizing remaining fructose and HMF in recovered LSP molten salt. In the recycle experiment, the 1st run was conducted with fructose (40 mg), LSP molten salts (2 g), and SBP (1 mL). After the 1st run, HMF extracted in SBP solvent (top layer) was carefully separated from a bottom layer of the aqueous salt solution. Then, the aqueous salt solution was dried overnight at 100° C. and analyzed for remaining fructose and HMF in dried salt. The recovered dried salt (2 g) was further used in the next recycle run with fresh fructose (40 mg) and SBP (1 mL). The amount of fructose conversion, HMF yield, and HMF selectivity were calculated after correction of remaining amount of fructose and HMF in dried salt.

It is noteworthy that LSP molten salt was recycled at least 3 times without losing its activity at 125° C., 30 min (FIG. 3). Thus, using molten salts possessing low eutectic point, such as LSP molten melts, could be regarded as one alternative process for the conversion of biomass-derived chemicals.

We claim:

1. A process for chemical transformation from saccharides, comprising:
   mixing a saccharide with a molten salt composition to form a mixture, wherein the molten salt composition comprises at least two alkali metal salts, wherein at least one of the alkali metal salts is selected from the group consisting of nitrates, nitrites, and carbonates, and wherein the molten salt composition has an eutectic point under 200° C.;
   heating and stirring the mixture;
   cooling the mixture; and
   extracting a product from the mixture.

2. The process according to claim 1, wherein the product is 5-Hydroxymethylfurfural (HMF).

3. The process according to claim 2, wherein the molten salt composition is in a liquid phase during the mixing; and the mixture is heated and stirred at a reaction temperature of 25° C. to 200° C. for 20 to 150 mins and then cooled to room temperature.

4. The process according to claim 2, wherein the saccharide is monosaccharides having 5 or 6 carbon atoms or disaccharides of two monosaccharides via 1, 4-glycosidic linkage or polysaccharides as polymers from monosaccharides with glycosidic bonds.

5. The process according to claim 4, wherein the saccharide is fructose, glucose, saccharide, inulin, cellobiose, cellulose, or starch.

6. The process according to claim 2, wherein the saccharide is in an amount up to 1 wt. %, 2 wt. %, 5 wt. %, 8 wt. %, or 10 wt. % based on a total weight of the molten salt composition.

7. The process according to claim 2, wherein the mixture is heated for 30-120 mins.

8. The process according to claim 2, wherein the reaction temperature is 115-155° C.

9. The process according to claim 2, wherein the mixture is heated at 135° C. for 30 mins.

10. The process according to claim 2, further comprising adding carbon monoxide, carbon dioxide, or oxygen to the resulting HMF for reaction.

11. The process according to claim 10, wherein the oxygen is added to the resulting HMF to obtain 2, 5-furandicarboxylic acid (FDCA).

12. A continuous process for production of 5-Hydroxymethylfurfural (HMF), comprising loading a reaction vessel with a molten salt composition, wherein the molten salt composition comprises at least two alkali metal salts, wherein at least one of the alkali metal salts is selected from the group consisting of nitrates, nitrites, and carbonates, and wherein the molten salt composition has an eutectic point under 200° C.;

pre-heating the molten salt composition to a desired reaction temperature at which it turns to a liquid phase;

feeding a saccharide into a reaction vessel;

heating the reaction vessel at the desired reaction temperature while consistently mixing the saccharide with the molten salt composition by stirring for a desired reaction time;

drawing a chemical product from the reaction vessel as a product stream into a vacuum distillation tower by a first vacuum pump; and cooling the product stream;

optionally adding carbon monoxide, carbon dioxide, or oxygen to the product stream; and extracting HMF product from the product stream and separating the HMF product via a second vacuum pump.

13. The process according to claim 12, wherein the HMF product comprises HMF, HMF dimer, 2, 5-furandicarboxylic acid, $C6^+$ chemical produced by addition of carbon monoxide or carbon dioxide through a double bond of HMF, or combinations thereof.

* * * * *